(12) United States Patent
Zhang

(10) Patent No.: US 12,403,117 B2
(45) Date of Patent: *Sep. 2, 2025

(54) STABLE PHARMACEUTICAL COMPOSITION CONTAINING NON-STEROIDAL ANTI-INFLAMMATORY DRUG DERIVATIVE

(71) Applicant: ZHEJIANG YUEJIA PHARMACEUTICALS CO., LTD, Deqing County (CN)

(72) Inventor: Jing Zhang, Shanghai (CN)

(73) Assignee: ZHEJIANG YUEJIA PHARMACEUTICALS CO., LTD, Deqing County (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/668,653

(22) Filed: May 20, 2024

(65) Prior Publication Data

US 2024/0299332 A1 Sep. 12, 2024

Related U.S. Application Data

(63) Continuation of application No. 18/312,466, filed on May 4, 2023, now Pat. No. 11,986,453, which is a continuation of application No. 16/758,880, filed as application No. PCT/CN2018/108622 on Sep. 29, 2018, now abandoned.

(30) Foreign Application Priority Data

Oct. 26, 2017 (CN) .......................... 201711014218.2

(51) Int. Cl.
*A61K 31/245* (2006.01)
*A61K 9/08* (2006.01)
*A61K 31/216* (2006.01)

(52) U.S. Cl.
CPC .............. *A61K 31/245* (2013.01); *A61K 9/08* (2013.01); *A61K 31/216* (2013.01)

(58) Field of Classification Search
CPC .. A61K 31/216; A61K 31/235; A61K 31/245; A61K 9/08; A61K 9/1635; A61K 9/1652; A61K 9/2054; A61P 29/00; G01K 7/14
See application file for complete search history.

(56) References Cited

U.S. PATENT DOCUMENTS

| | | | |
|---|---|---|---|
| 3,341,416 | A | 9/1967 | Anderson et al. |
| 3,365,483 | A | 1/1968 | Jerzmanowska et al. |
| 4,970,081 | A | 11/1990 | Frisbee |
| 6,951,657 | B1 | 10/2005 | Zuccarelli et al. |
| 9,718,766 | B2 | 8/2017 | Yu et al. |
| 2009/0238763 | A1 | 9/2009 | Yu et al. |
| 2016/0002157 | A1 | 1/2016 | Yu et al. |
| 2024/0360073 | A1* | 10/2024 | Zhang .................. C07C 291/04 |

FOREIGN PATENT DOCUMENTS

| | | |
|---|---|---|
| CN | 101484415 A | 7/2009 |
| CN | 101489985 A | 7/2009 |
| CN | 203282772 U | 11/2013 |
| CN | 104276962 A | 1/2015 |
| CN | 105143174 A | 12/2015 |
| CN | 106146326 A | 11/2016 |
| JP | 2009542797 A | 12/2009 |
| JP | 2009543857 A | 12/2009 |
| WO | 9317716 | 9/1993 |
| WO | 2008007171 A1 | 1/2008 |
| WO | 2008010025 A1 | 1/2008 |
| WO | 2014138708 A1 | 9/2014 |
| WO | 2014139161 A1 | 9/2014 |
| WO | 2016155468 A1 | 10/2016 |

OTHER PUBLICATIONS

International Search Report and Written Opinion issued for International Patent Application No. PCT/CN2018/108622, dated Jan. 7, 2019, 9 pages.
First Examination Report issued for Indian Patent Application No. 202017021975, dated Oct. 29, 2020, 5 pages.
Supplementary European Search Report issued for European Patent Application No. 18871568.4, dated Jun. 28, 2021, 10 pages.
Office Action issued for Japanese Patent Application No. 2020-523346, dated Apr. 19, 2021, 6 pages.
Garg. Drug Delivery, 2015, 22(8), 969-987 (Year: 2015).
Sanchez-Regana et al. (Actas Dermosifiliogr 2013, 104(9), 738-756). (Year: 2013).
USP, (https://www.in.gov/health/files/USP1160_Calculations%20in%20Prescription %20Compounding.pdf, 2012). (Year: 2012).
Hemchand et al. (https://www.farmavita.net/documents/Tablet%20coating.pdf 2009). (Year: 2009).
Breneman (Abbott Laboratories, 2011, p. 1-30). (Year: 2011).
Manukondakeerthi et al. (Asian J of Research in Pharmaceutical Sciences, 2014, p. 1-18). (Year: 2014).
WO2016155468A1—English Translation (Year: 2016).
Zu, 2013 (english translation of CN 203282772) (Year: 2013).
"Chapter V Antipyretic and Analgesic Drugs and Non-steroidal Anti-inflammatory Drugs," p. 151, Learning Essentials of Basic Pharmacology, Editor-in-Chief Zhang Bin et al., 2010 (4 pages with English translation), Cited in First Office Action issued for Chinese Patent Application No. 201880066950.0, dated Feb. 14, 2023.
First Office Action issued for Chinese Patent Application No. 201880066950.0, dated Feb. 14, 2023, 13 pages including English translation.

(Continued)

*Primary Examiner* — Umamaheswari Ramachandran
(74) *Attorney, Agent, or Firm* — HSML P.C.

(57) ABSTRACT

A stable pharmaceutical composition containing a non-steroidal anti-inflammatory drug derivative, at least comprising a separated solid part and liquid part, the solid part comprising a therapeutically effective dose of non-steroidal anti-inflammatory drug derivative and the liquid part being a pharmaceutically acceptable solvent. After a long-term stability study (25° C.±2° C., 12 months), the stability of the solid part was good, and met the requirements of the pharmaceutical industry.

20 Claims, No Drawings

(56) References Cited

OTHER PUBLICATIONS

Notice on Grant of Patent Right for Invention issued for Chinese Patent Application No. 201880066950.0, dated Apr. 24, 2023, 3 pages including partial English translation.
Communication pursuant to Article 94(3) EPC issued for European Patent Application No. 18871568.4, dated Jan. 23, 2024, 7 pages.

* cited by examiner

STABLE PHARMACEUTICAL COMPOSITION CONTAINING NON-STEROIDAL ANTI-INFLAMMATORY DRUG DERIVATIVE

TECHNICAL FILED

The invention relates to the field of chemical pharmacy, in particular to a stable pharmaceutical composition containing a non-steroidal anti-inflammatory drug derivative.

BACKGROUND

Non-steroidal anti-inflammatory drugs are a class of anti-inflammatory drugs that do not contain a steroid structure, including aspirin, salicylic acid, acetaminophen, indomethacin, naproxen, nabumetone, diclofenac, ibuprofen, nimesulide, rofecoxib, celecoxib, etc. Non-steroidal anti-inflammatory drugs have antipyretic, analgesic, anti-inflammatory, anti-rheumatic, and anti-coagulant effects, etc, and are widely used in clinical practice for alleviating osteoarthritis, rheumatoid arthritis, a variety of fevers and various pain symptoms. Non-steroidal anti-inflammatory drugs have antipyretic, analgesic and anti-inflammatory effects by inhibiting the synthesis of prostaglandins. The analgesic site of non-steroidal anti-inflammatory drugs is mainly peripheral. Its analgesic mechanisms include: 1) inhibition of prostaglandin synthesis; 2) inhibition of lymphocyte activity and differentiation of activated T-lymphocytes, thereby reducing stimulation to afferent nerve endings; 3) directly affecting nociceptors, thereby preventing the formation and release of pain-causing substances. Most non-steroidal anti-inflammatory drugs have anti-inflammatory effects. They have anti-inflammatory effects by inhibiting the synthesis of prostaglandins, inhibiting the accumulation of white blood cells, reducing the formation of bradykinin, and inhibiting the aggregation of platelets. Non-steroidal anti-inflammatory drugs can inhibit the occurrence, development and metastasis of tumors, and have synergistic effects with other anti-tumor drugs. Among them, aspirin and ibuprofen are the most classic non-steroidal anti-inflammatory drugs.

Aspirin, also known as acetylsalicylic acid, was first synthesized in 1853 and was used in clinical treatment in 1899. Aspirin has a variety of drug effects. It can relieve headaches in a short term through vasodilation, so it can be used for analgesia and antipyresis. Aspirin is the drug of choice for the treatment of rheumatic fever. After taking the drug, it can relieve fever and reduce inflammation, improving joint symptoms and reducing blood sedimentation. In addition to rheumatic arthritis, this drug is also used to treat rheumatoid arthritis, and it can improve symptoms and create conditions for further treatment. In addition, aspirin is used for skeletal muscle pain associated with osteoarthritis, ankylosing spondylitis, juvenile arthritis and other non-rheumatic inflammation, and it can also relieve symptoms. Aspirin has an inhibitory effect on platelet aggregation, which can prevent thrombosis. It can be used clinically to prevent transient ischemic attack, myocardial infarction, atrial fibrillation, thrombosis after artificial heart valve surgery or other surgeries, and can also be used to treat unstable angina. Aspirin can also be used to relieve mucocutaneous lymph node syndrome (Kawasaki disease). It was also found that aspirin played a role in preventing colon cancer, rectal cancer, and esophageal cancer. Therefore, the therapeutic usage of aspirin is very valuable.

Ibuprofen, also known as α-methyl-4-(2-methylpropyl) phenylacetic acid, is the only anti-fever drug for children recommended by both the World Health Organization and the US FDA, and is recognized as the preferred anti-inflammatory drug for children. Ibuprofen has anti-inflammatory, analgesic, and antipyretic effects, and is suitable for the treatment of mild to moderate migraine attacks, migraine prevention, chronic paroxysmal migraine headaches, strenuous and menstrual headaches, rheumatic arthritis, rheumatoid arthritis, osteoarthritis, ankylosing spondylitis, neuritis, etc. Ibuprofen reduces the synthesis of prostaglandins by inhibiting cyclooxygenase, blocks the release of inflammatory mediators, and produces anti-inflammatory and analgesic effects. At the same time, it acts as an antipyretic through the hypothalamic body temperature regulation center.

However, oral non-steroidal anti-inflammatory drugs easily result in adverse gastrointestinal reactions. The main symptoms include indigestion, stomach and duodenal bleeding, gastric ulcers, gastritis, etc. Therefore, researchers have been trying to study non-steroidal anti-inflammatory drug derivatives suitable for other administration routes in order to reduce or avoid the adverse gastrointestinal reactions caused by oral administration of non-steroidal anti-inflammatory drugs. Chinese patents CN101484415B and CN101489985B respectively disclose a water-soluble aspirin prodrug (an acetylsalicylic acid derivative) and an ibuprofen prodrug (an ibuprofen derivative). The drugs can be introduced into the body through transdermal administration, avoiding the gastrointestinal adverse reactions caused by ordinary oral administration of non-steroidal anti-inflammatory drugs.

Obtaining stable medicaments from these compounds is a problem that the pharmaceutical industry must solve.

DISCLOSURE OF INVENTION

In one aspect of the present invention, a stable pharmaceutical composition containing a non-steroidal anti-inflammatory drug derivative is provided. The pharmaceutical composition includes at least a separated solid portion and a separated liquid portion, wherein the solid portion includes a therapeutically effective amount of a pharmaceutically acceptable salt of a compound represented by general Formula 1, and the liquid portion includes a pharmaceutically acceptable solvent, wherein, Formula 1

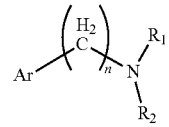

Ar— represents

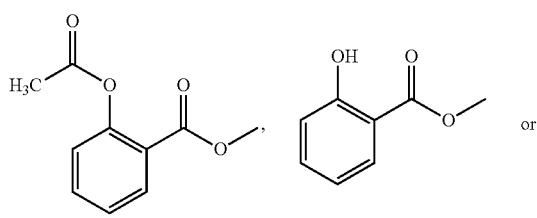

-continued

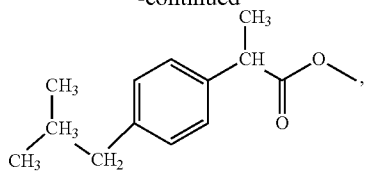

$R_1$ represents H, C1 alkyl, C2 alkyl, C3 alkyl, C4 alkyl, C5 alkyl or C6 alkyl, preferably methyl or ethyl, $R_2$ represents H, C1 alkyl, C2 alkyl, C3 alkyl, C4 alkyl, C5 alkyl or C6 alkyl, preferably methyl or ethyl, n represents 1, 2, 3, 4, 5, 6, 7, 8, 9 or 10, preferably 1 or 2.

In a preferred embodiment, the compound represented by general Formula 1 is selected from the group consisting of the following compounds:

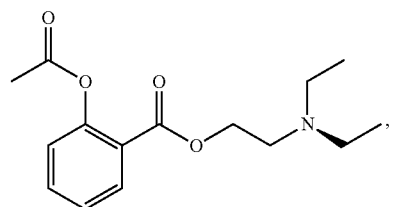

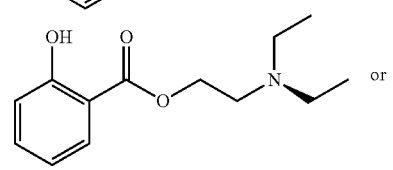

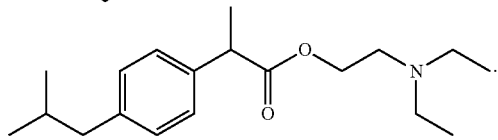

In a preferred embodiment, the pharmaceutically acceptable salt of the compound represented by general Formula 1 is a salt formed by the compound represented by general Formula 1 with an inorganic acid or an organic acid, preferably a salt formed by the compound represented by general Formula 1 with hydrochloric acid, hydrobromic acid, hydrofluoric acid, hydroiodic acid, phosphoric acid, acetic acid, oxalic acid, citric acid or thiocyanic acid.

In a preferred embodiment, the pharmaceutically acceptable salt of the compound represented by general Formula 1 comprises:

2-(diethylamino)-ethyl-2-acetoxybenzoate hydrochloride, salicylic acid-(2-diethylaminoethyl ester) hydrochloride, or 2-(diethylamino)-ethyl-2-(4-isobutylphenyl) propionate hydrochloride.

Alternatively, the present invention provides a stable pharmaceutical composition containing a non-steroidal anti-inflammatory drug derivative. The pharmaceutical composition includes at least a separated solid portion and a separated liquid portion, wherein the solid portion includes a therapeutically effective amount of a compound represented by general Formula 2, and the liquid portion includes a pharmaceutically acceptable solvent, wherein,

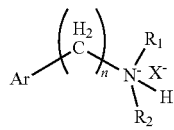

Formula 2

Ar— represents

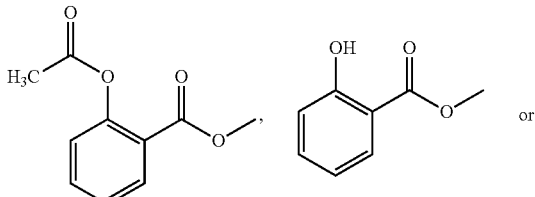

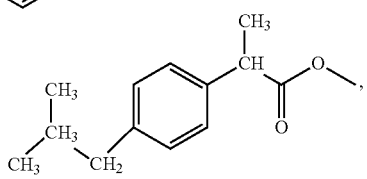

$R_1$ represents H, C1 alkyl, C2 alkyl, C3 alkyl, C4 alkyl, C5 alkyl or C6 alkyl, preferably methyl or ethyl, $R_2$ represents H, C1 alkyl, C2 alkyl, C3 alkyl, C4 alkyl, C5 alkyl or C6 alkyl, preferably methyl or ethyl, $X^-$ represents an anion, n represents 1, 2, 3, 4, 5, 6, 7, 8, 9 or 10, preferably 1 or 2.

In a preferred embodiment, X represents a monovalent anion, more preferably $Cl^-$, $Br^-$, $F^-$, $I^-$, $AcO^-$, oxalate, dihydrogen phosphate, citrate or thiocyanate group.

In a preferred embodiment, the compound represented by general Formula 2 is selected from the group consisting of the following compounds:

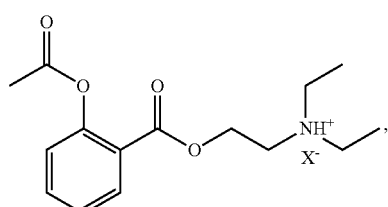

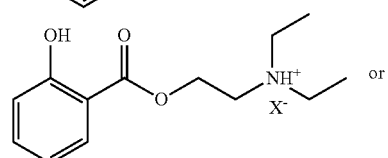

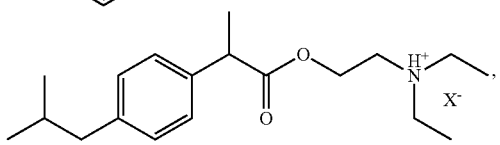

wherein, $X^-$ represents an anion, preferably a monovalent anion, more preferably $Cl^-$, $Br^-$, $F^-$, $I^-$, $AcO^-$, oxalate, dihydrogen phosphate, citrate and thiocyanate group.

In a preferred embodiment, the compound represented by general Formula 2 comprises:
2-(diethylamino)-ethyl-2-acetoxybenzoate hydrochloride, salicylic acid-(2-diethylaminoethyl ester) hydrochloride, or 2-(diethylamino)-ethyl-2-(4-isobutylphenyl) propionate hydrochloride.

It should be noted that the compound represented by general Formula 2 is a pharmaceutically acceptable salt of the compound represented by general Formula 1. Therefore, the terms of "a pharmaceutically acceptable salt of a compound represented by general Formula 1" and "a compound represented by general Formula 2" herein are used interchangeably.

In a preferred embodiment, the mass ratio of the solid portion to the liquid portion is from 0.1:100 to 40:100, more preferably from 0.5:100 to 20:100, most preferably from 1:100 to 10:100. In another preferred embodiment, the mass ratio of the pharmaceutically acceptable salt of the compound represented by general Formula 1 to the liquid portion (the pharmaceutically acceptable solvent) is from 0.1:100 to 40:100, more preferably from 0.5:100 to 20:100, most preferably from 1:100 to 10:100.

In a preferred embodiment, the pharmaceutically acceptable solvent is selected from the group consisting of sterile water, decarbonated water, ethanol, sorbitol aqueous solution, and physiological saline.

In a preferred embodiment, the dosage form of the solid portion is selected from the group consisting of powders, granules, pills, tablets and capsules.

In a preferred embodiment, the solid portion further includes a pharmaceutically acceptable binder.

In a preferred embodiment, the pharmaceutically acceptable binder is selected from the group consisting of hypromellose, carbomer, ethyl cellulose, hydroxypropyl cellulose, vinyl cellulose, starch (more preferably pregelatinized starch), polyvinylpyrrolidone.

In a preferred embodiment, the pharmaceutically acceptable salt of the compound represented by general Formula 1 forms particles with the pharmaceutically acceptable binder.

In a preferred embodiment, the mass ratio of the pharmaceutically acceptable salt of the compound represented by general Formula 1 to the pharmaceutically acceptable binder is from 100:0.05 to 100:10, more preferably from 100:1 to 100:5, most preferably from 100:1 to 100:2.

In a preferred embodiment, the repose angle of the powder or granules of the invention does not exceed 40°, preferably does not exceed 35°, more preferably does not exceed 30°.

In a preferred embodiment, the particles can pass through a 10-mesh screen but cannot pass through a 60-mesh screen. In another preferred embodiment, the powder can pass through an 80-mesh screen. In a preferred embodiment, the solid portion is stored in a hermetic, pharmaceutically acceptable packaging material.

In a preferred embodiment, the pharmaceutically acceptable packaging material is selected from the group consisting of a low density polyethylene film, a low density polyethylene bag, a high density polyethylene film, a low density polyethylene bottle, a high density polyethylene bottle, a polypropylene bottle, a poly(ethylene terephthalate) bottle, a polyester/aluminum/polyethylene composite bag, a glass bottle, or a combination thereof.

In a preferred embodiment, the pharmaceutical composition further comprises a pharmaceutical spray device, a medicinal dropper, a medicinal soft brush, or a combination thereof.

In a preferred embodiment, when the pharmaceutical composition is used, the solid portion is mixed with the liquid portion to form a spray, a drop, or an inunction.

Another aspect of the present invention provides a method of making the particles, comprising the steps of:
(1) formulating a binder solution;
(2) mixing the pharmaceutically acceptable salt of the compound represented by general Formula 1 with a dry powder of a binder at a given ratio, then adding the binder solution prepared in step (1) to uniformly mix, thereby obtaining a soft material;
(3) drying the soft material;
(4) granulating and selecting the particles that can pass through a 10-mesh screen but cannot pass through a 60-mesh screen.

In a preferred embodiment, the concentration of the binder solution formulated in step (1) is 0.1 w/w % to 3.0 w/w %.

In a preferred embodiment, the mass ratio of the pharmaceutically acceptable salt of the compound represented by general Formula 1 in step (2) to the dry powder of the binder is from 100:0.1 to 100:5.

In a preferred embodiment, the mass ratio of the binder solution added in step (2) to the pharmaceutically acceptable salt of the compound represented by general Formula 1 is from 1:100 to 10:100.

In a preferred embodiment, the drying temperature in step (3) is 55-65° C.

In a preferred embodiment, the drying time in step (3) is 4-6 hours.

The non-steroidal anti-inflammatory drug derivative according to the invention has a number of beneficial effects. For example, since the non-steroidal anti-inflammatory drug derivative cannot be stably present in the solvent (the solution state is not stable), the solid portion of the drug needs to be stored separately from the solvent. More preferably, the solid portion of the drug can be stored in a suitable pharmaceutical packaging material. Thus, the stability of the drug can be remarkably improved. When the solid portion of the pharmaceutical composition comprises particles, the repose angle of the particles is not more than 30 degrees, the fluidity is good without sticking, the particles can be rapidly dissolved in the solvent, and the dissolving operation during use by a patient is facilitated. After the solid portion of the pharmaceutical composition is dissolved in the solvent, the drug can be administered in a transdermal administration mode, and gastrointestinal adverse reactions (bleeding and the like) and systemic exposure caused by oral administration are avoided. In addition, after the solid portion is mixed with the liquid portion, multiple external medicine dosage forms can be formed, and the use by a patient is facilitated.

Embodiments of Invention

In particular, the present disclosure provides a stable pharmaceutical composition containing a non-steroidal anti-inflammatory drug derivative, wherein the pharmaceutical composition includes at least a separated solid portion and a separated liquid portion, wherein the solid portion includes a therapeutically effective amount of a pharmaceutically acceptable salt of a compound represented by general Formula 1, and the liquid portion includes a pharmaceutically acceptable solvent, wherein,

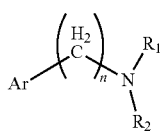

Ar— represents

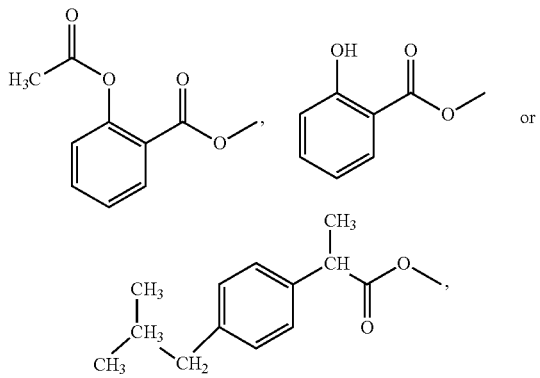

$R_1$ represents H or $C_1$-$C_6$-alkyl, preferably $C_1$-$C_6$-alkyl, more preferably $C_1$-$C_4$-alkyl, even more preferably $C_1$-$C_3$-alkyl, most preferably methyl or ethyl, $R_2$ represents H or $C_1$-$C_6$-alkyl, preferably $C_1$-$C_6$-alkyl, more preferably $C_1$-$C_4$-alkyl, even more preferably $C_1$-$C_3$-alkyl, most preferably methyl or ethyl, n represents 1, 2, 3, 4, 5, 6, 7, 8, 9 or 10; preferably, n is a natural number of less than or equal to 6; more preferably, n is a natural number of less than or equal to 4; most preferably, n is a natural number of less than or equal to 3.

As used herein, the term "comprise/include at least . . . " means that the pharmaceutical composition can also contain any other components, and these components may be present in any amount, as long as the amounts of the components are acceptable to human body, and for the purposes of the present invention, the activity of the active ingredients in the pharmaceutical composition is not adversely affected.

As used herein, the term "pharmaceutically acceptable salts" preferably refers to relatively non-toxic, inorganic or organic acid addition salts of the compounds of general Formula 1. Examples of the pharmaceutically acceptable salts comprise salts formed by the compounds represented by general Formula 1 with inorganic acids, or organic acids. The inorganic acids include, but are not limited to, hydrochloric acid, hydrobromic acid, hydrofluoric acid, hydroiodic acid, sulfuric acid, disulfuric acid, phosphoric acid or nitric acid. The organic acids include, but are not limited to, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphor acid, cinnamic acid, cyclopentane propionic acid, a glucaric acid, 3-hydroxy-2-naphthoic acid, nicotinic acid, dihydroxynaphthalenic acid, pectic acid, persulfuric acid, 3-phenylpropionic acid, picric acid, pivalic acid, 2-hydroxyethanesulfonic acid, itaconic acid, sulfamic acid, trifluoromethane sulfonic acid, dodecyl sulfuric acid, ethyl sulfonic acid, benzene sulfonic acid, p-toluenesulfonic acid, methanesulfonic acid, 2-naphthalene sulfonic acid, naphthalene disulfonic acid, camphor sulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptonic acid, glycerophosphoric acid, aspartic acid, sulfosalicylic acid, semi-sulfuric acid or thiocyanic acid. Preferably, the compound represented by general Formula 1 forms a salt with hydrochloric acid, hydrobromic acid, hydrofluoric acid, hydroiodic acid, phosphoric acid, acetic acid, oxalic acid, citric acid or thiocyanic acid.

The term "$C_1$-$C_6$-alkyl" refers to a straight or branched saturated monovalent hydrocarbon radical having 1, 2, 3, 4, 5 or 6 carbon atoms. Examples of $C_1$-$C_6$-alkyl include methyl, ethyl, propyl, butyl, pentyl, hexyl, isopropyl, isobutyl, sec-butyl, tert-butyl, iso-pentyl, 2-methyl-butyl, 1-methyl-butyl, 1-ethylpropyl, 1,2-dimethylpropyl, neopentyl, 1,1-dimethylpropyl, 4-methylpentyl, 3-methylpentyl, 2-methyl-pentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethyl-butyl, preferably methyl, ethyl, propyl, isopropyl, butyl, sec-butyl or tert-butyl, more preferably methyl or ethyl.

According to the Chinese patents CN101484415B and CN101489985B, the pharmaceutical compositions of the present invention may be suitable for the indications that can be treated with non-steroidal anti-inflammatory agents (such as aspirin, ibuprofen), including, but not limited to, pain, fever, inflammation, rheumatism, arthritis, thrombus, cancer, stroke, Alzheimer's disease, diabetes, diabetic complications, cardiovascular diseases, cerebrovascular diseases and the like.

The non-steroidal anti-inflammatory drug derivatives of the present invention may be prepared according to Chinese patents CN101484415B and CN101489985B, U.S. Pat. No. 3,365,483 or other references. Such prodrug derivatives have the advantages that, for example, they can be administered transdermally into the body, thus avoiding the gastrointestinal adverse reactions caused by ordinary oral administration of non-steroidal anti-inflammatory drugs. Therefore, the drugs are preferably used in a solution dosage form for transdermal administration into the body. However, the inventors have found that the non-steroidal anti-inflammatory drug derivative cannot stably exist in a solvent (the solution is not stable). Thus, the solid portion of the drug and the solvent need to be stored separately. More preferably, the solid portion of the drug may be stored in a sealed medicinal packaging material, thereby obviously improving the stability of the drug.

In a preferred embodiment, the mass ratio of the solid portion and the liquid portion is from 0.1:100 to 40:100, more preferably from 0.5:100 to 20:100, and most preferably from 1:100 to 10:100.

In a preferred embodiment, the solid portion of the pharmaceutical composition contains powders, granules, pills, tablets, or capsules of a pharmaceutically acceptable salt of the compound represented by general Formula 1.

In a preferred embodiment, the solid portion of the pharmaceutical composition contains particles formed from a pharmaceutically acceptable salt of the compound represented by general Formula 1 with a pharmaceutically acceptable binder.

The term "pharmaceutically acceptable binder" refers to sticky solid powders or thick liquid which can enable aggregation and bonding of a non-sticky or less sticky material into granules or compression molding, and is compatible with the active ingredient, a non-steroidal anti-inflammatory drug derivative (i.e. a pharmaceutically acceptable salt of the compound represented by general Formula 1), in a pharmaceutical composition of the present invention. That is, it may be blended with a drug without reducing the activity of the drug greatly.

In a preferred embodiment, the pharmaceutically acceptable binder is selected from the group consisting of hypromellose, carbomer, ethyl cellulose, hydroxypropyl cellulose, vinyl cellulose, starch (more preferably pregelatinized starch), polyvinyl pyrrolidone. When the solid portion of the pharmaceutical composition contains particles formed from a pharmaceutically acceptable salt of the compound represented by general Formula 1 with a pharmaceutically acceptable binder, the particles are mixed with and dissolved in a pharmaceutically acceptable solvent (e.g., sterile water) to form a film after coating and drying. The film is not easy to fall off, and the patient can conveniently attach the drug onto the skin for absorbing.

A common adhesive (e.g., hypromellose, carbomer, ethyl cellulose, hydroxypropyl cellulose, vinyl cellulose, starch or polyvinylpyrrolidone) is mixed with a pharmaceutically acceptable salt of the compound represented by general Formula 1 of the present invention, and then the mixture is wet granulated to form particles. The particles are then mixed with and dissolved in a pharmaceutically acceptable solvent (e.g., sterile water). The result shows that the particles formed from hypromellose with the pharmaceutically acceptable salt of the compound represented by general Formula 1 have best solubility, and a clear solution is formed. A transparent film is formed after coating and drying, which is not easy to fall off. The patient can conveniently adhere the drug to the skin for absorbing. Thus, in an optimal embodiment, the pharmaceutically acceptable binder is hypromellose.

In a preferred embodiment, the mass ratio of the pharmaceutically acceptable salt of the compound represented by general Formula 1 to the pharmaceutically acceptable binder is from 100:0.05 to 100:10, more preferably from 100:1 to 100:5, and most preferably from 100:1 to 100:2.

The "repose angle" formed by stacking the powders or particles reflects its fluidity. The term "repose angle" generally refers to the maximum angle formed by the free slope of the layer of the stacked powders or particles and the horizontal plane. The smaller the repose angle, the smaller the friction between the powders or particles, and the better the fluidity. Better fluidity is more convenient for dissolution and use of the powders or particles. Methods for measuring the repose angle are well known to those skilled in the art. The repose angle is measured by an "injection method" in the examples of the invention, that is, the particles flow out of the funnel and fall on the plane to form a cone, and the base angle is the repose angle.

In a preferred embodiment, the repose angle of the powders or particles is less than or equal to 40°, more preferably less than or equal to 35°, and even more preferably less than or equal to 30°.

In a preferred embodiment, the solid portion of the pharmaceutical composition of the present invention is stored in a sealed, pharmaceutically acceptable packaging material.

The term "pharmaceutically acceptable packaging material" refers to such a packaging material that the container/sealing material and the content therein have no severe interaction. That is, the interaction, if any, does not result in a change in product activity and stability, or creates a risk of toxicity. Under normal storage/use condition, any interaction between the package material and the product does not result in unacceptable variations in product quality or packaging.

The pharmaceutically acceptable packaging material includes, but are not limited to, low density polyethylene films, low density polyethylene bags, high density polyethylene films, low density polyethylene bottles, high density polyethylene bottles, polypropylene bottles, poly(ethylene terephthalate) bottles, polyester/aluminum/polyethylene composite films, polyester/aluminum/polyethylene composite bags, glass bottles, or combinations thereof.

In a preferred embodiment, the pharmaceutically acceptable packaging material is a combination of a high density polyethylene bottle and a polyester/aluminum/polyethylene composite bag.

In a preferred embodiment, the liquid portion of the pharmaceutical composition of the present invention comprises a pharmaceutically acceptable solvent.

The pharmaceutically acceptable solvents include, but are not limited to, sterile water, decarbonated water, ethanol, sorbitol aqueous solution, physiological saline, and the like.

In a preferred embodiment, the pharmaceutical composition further comprises a pharmaceutical spray device, a medicinal dropper, a medicinal soft brush, or a combination thereof.

In a preferred embodiment, the solid portion of the pharmaceutical composition, when used, mixes with the liquid portion to form a spray, a drop, or an inunction.

In a preferred embodiment, the solid portion (particles) of the pharmaceutical composition is packaged with a high density polyethylene bottle and then placed in a composite bag of polyester/aluminum/polyethylene for drug packaging. The liquid portion comprises sterile water as a solvent (stored in a pharmaceutical glass bottle or a pharmaceutical polyethylene plastic bottle). The solid portion and the liquid portion are placed in a plastic tray with a pharmaceutical spray device, such as a pharmaceutical spray pump, and then are together placed in a white card carton. It should be noted that in order to facilitate the use by a patient, the particles and the solvent may be packaged in advance in a given ratio, such as 5 g of particles and 50 mL of sterile water. When used by a patient, 5 g of the particles are all dissolved in 50 mL of sterile water to form a 10% aqueous solution which is then used with a pharmaceutical spray pump to form a spray (the aqueous solution is for use within a specified period of time, for example, 1-2 weeks).

The present invention also provides a method of making the particles, comprising the steps of:
  (1) formulating a binder solution;
  (2) mixing a pharmaceutically acceptable salt of the compound represented by general Formula 1 with the binder solution formulated in step (1).

The inventors have discovered that adding a binder (e.g., hypromellose) solution directly to the pharmaceutically acceptable salt of the compound represented by general Formula 1 of the present invention is difficult to produce desired particles, and the obtained particles are loose, fragile and easy to agglomerate. Thus, the inventors have improved granulation methods by mixing a pharmaceutically acceptable salt of the compound represented by general Formula 1 of the present invention with a dry powder of a binder (e.g., hypromellose), and then adding a binder (e.g., hypromellose) solution to mix, thereby obtaining the desired particles.

In particular, the present invention provides another method of making the particles, the method comprising the steps of:

(1) formulating a binder solution;
(2) mixing the pharmaceutically acceptable salt of the compound represented by general Formula 1 with a dry powder of a binder at a given ratio, then adding the binder solution prepared in the step (1) to uniformly mix, thereby obtaining a soft material;
(3) drying the soft material;
(4) granulating and selecting the particles that can pass through a 10-mesh screen but cannot pass through a 60-mesh screen.

In a preferred embodiment, the content of the binder solution formulated in step (1) is 0.1 w/w % to 3.0 w/w %.

In a preferred embodiment, the mass ratio of the pharmaceutically acceptable salt of the compound represented by general Formula 1 to the dry powder of the binder in step (2) is from 100:0.1 to 100:5.

In a preferred embodiment, the mass ratio of the binder solution added in step (2) to the pharmaceutically acceptable salt of the compound represented by general Formula 1 is from 1:100 to 10:100.

In a preferred embodiment, the drying temperature in step (3) is 55-65° C.

In a preferred embodiment, the drying time in step (3) is 4-6 hours.

As used herein, the term "comprise the steps of: . . . " means that in addition to the listed steps, the method may include any other step to help or facilitate the completion of the method. For example, a pharmaceutically acceptable salt of the compound represented by general Formula 1 can be screened before step (2), thereby facilitating the subsequent granulation step.

In a preferred embodiment, the method comprises the following steps of:
(1) screening a pharmaceutically acceptable salt of the compound represented by general Formula 1 of the present invention with an 80-mesh screen;
(2) formulating a solution of hypromellose at a given concentration (preferably 1-3 w/w %, more preferably 1.5 w/w %), standing overnight at room temperature for standby;
(3) mixing the pretreated pharmaceutically acceptable salt of the compound represented by general Formula 1 with the dry powder of hypromellose (preferably the mass ratio is 100:1.5), then adding the hypromellose solution prepared in step (2) (the mass ratio of the compound to the dry powder of the binder is from 100:1 to 100:5, more preferably from 100:1 to 100:2, and even more preferably from 100:1.5 to 100:1.7), and uniformly mixing to produce a soft material which is then pressed through 14-mesh screen;
(4) drying the soft material (preferably, the drying temperature is 60° C.; preferably, the drying time is less than 12 hours, more preferably 4 to 6 hours);
(5) granulating and selecting particles (preferably, selecting particles that can pass through a 10-mesh screen but cannot pass through a 60-mesh screen).

The present invention also provides a method of making a tablet, comprising the steps of:
(1) formulating a binder solution;
(2) mixing the pharmaceutically acceptable salt of the compound represented by general Formula 1 with a flowing aid (such as talcum powder), adding the binder solution prepared in step (1), and mixing uniformly to obtain a soft material;
(3) drying the soft material;
(4) tabletting.

It should be noted that any combination of the techniques described herein may be implemented.

The invention is further illustrated with specific examples. It should be understood that these examples are merely illustrative of the invention and are not intended to limit the scope of the invention. In the methods of the following examples, if the specific conditions are not specified, conventional conditions or conditions as suggested by the manufacturer may be applicable. All percentages, ratios, proportions, or parts are by weight unless otherwise specified.

Units in a weight/volume percentage in the present invention are well known to those skilled in the art. For example, the weight/volume percentage may refer to the weight (grams) of a solute in 100 milliliters of a solution.

Unless otherwise specified, all technical and scientific terms used herein have the same meaning as commonly understood by one of ordinary skill in the art. In addition, any methods and materials similar or equivalent to those described may be employed in the present invention. The preferred embodiments and materials described herein are exemplary only.

EXAMPLES

Example 1: Preparation of 2-(Diethylamino)-Ethyl-2-Acetoxybenzoate Hydrochloride Using toluene as the solvent and N, N-dimethylformamide as the catalyst, aspirin and sulfoxide chloride were reacted at an equivalent ratio of 1:1.1 at a reaction temperature of 50° C. for 2 hours to produce o-acetylsalicyloyl chloride. Then, diethylaminoethanol and the acylation product o-acetylsalicyloyl chloride were reacted at an equivalent ratio of 1:1 at a reaction temperature of 25° C. for 4 hours, producing 2-(diethylamino)-ethyl 2-acetoxybenzoate. The aqueous phase was extracted with methyl tert-butyl ether, and the aqueous phase was taken into an ice bath. Sodium bicarbonate was added to adjust the pH to 7-8, and then isopropyl acetate was used as the extractant to extract the aqueous phase. The isopropyl acetate phase was taken. Isopropyl acetate was used as the solvent in the salt formation process, and then the amount of hydrogen chloride gas introduced was strictly controlled, so that the pH of the reaction solution was about 3.5. After the completion of the reaction, 2-(diethylamino)ethyl 2-acetoxybenzoate hydrochloride crude raw material was obtained.

Under heating and reflux, anhydrous acetonitrile was continuously added to the crude raw material of 2-(diethylamino)ethyl 2-acetoxybenzoate hydrochloride with stirring, until 2-(diethylamino)ethyl 2-acetoxybenzoate hydrochloride was completely dissolved. The final mass/volume ratio of the crude raw material of 2-(diethylamino)ethyl 2-acetoxybenzoate hydrochloride to anhydrous acetonitrile is 1:4. After slowly cooling to 25° C., white crystals were precipitated, and the solid was vacuum-dried after suction filtration.

The physical and chemical properties of the synthesized crystals of 2-(diethylamino)-ethyl-2-acetoxybenzoate hydrochloride are shown in Table 1.

TABLE 1

| Physical and Chemical Properties | Description |
|---|---|
| Morphology | White or white-like powders |
| Melting point | 136.0-139.0° C. |
| Repose angle | 42° |
| Solubility | This product is extremely soluble in water; very soluble in chloroform or methanol; soluble in ethanol; slightly soluble in acetone; insoluble in ethyl acetate and ether. |
| Acidity | The pH value of the 2% aqueous solution of this product at 25 ± 0.5° C. is 4.0-6.0 |
| Dissociation constant | 8.82 |

The synthesized 2-(diethylamino)-ethyl-2-acetoxybenzoate hydrochloride crystals were taken for NMR characterization, using Bruker AV-500 Superconducting NMR instrument, at a temperature of 300.0K. The solvent was $CDCl_3$. The characteristic data obtained are shown below, proving that the structure of the obtained product is consistent with 2-(diethylamino)-ethyl-2-acetoxybenzoate hydrochloride.

$^{13}$C NMR (400 MHZ, $CDCl_3$): δ8.49, 20.92, 47.17, 49.74, 58.80, 122.03, 123.73, 126.05, 131.15, 134.45, 150.73, 163.52, 169.45.

$^1$H NMR (400 MHZ, $CDCl_3$): δ1.42 (t, 6H, J=7.5 Hz), 2.35 (s, 3H), 3.23 (m, 4H), 3.42 (m, 2H), 4.85 (t, 2H, J=5.5 Hz), 7.14 (d, 1H, J=8.0 Hz), 7.34 (dd, 1H, J=8.0 Hz), 7.61 (dd, 1H, J=7.5 Hz), 8.00 (d, 1H, J=8.0 Hz), 12.54 (s, 1H).

Example 2: Stability of Aqueous Solution of 2-(Diethylamino)-Ethyl-2-Acetoxybenzoate Hydrochloride 5 g of 2-(diethylamino)-ethyl-2-acetoxybenzoate hydrochloride prepared in Example 1 was dissolved in 50 mL of sterile water and placed at 2-8° C. Samples were taken on day 0, month 0.5, month 1, month 2 and month 3 to detect the contents of the main drug and specific impurities (salicylic acid-(2-diethylaminoethyl ester) hydrochloride, acetylsalicylic acid, salicylic acid) and related substances, wherein the content of the main drug and specific impurities were detected by high-performance liquid chromatography (external standard method), and the related substances were detected by high-performance liquid chromatography (principal component self-control method without correction factors). The conditions of HPLC were as follows:

Column: Inertsil ODS-3 (250×4.6 mm, 5 μm) or equivalent

Flow rate: 1.0 ml/min

Column temperature: 33° C.

Wavelength: 276 nm, 303 nm

Injection volume: 10 μl

Mobile phase: water (15 ml of triethylamine+3.5 ml of 10% tetrabutylammonium hydroxide, adding water to 1000 ml): methanol: glacial acetic acid (63:27:10).

The results of the stability study showed that after the aqueous solution of 2-(diethylamino)-ethyl-2-acetoxybenzoate hydrochloride was placed at 2-8° C. for 3 months, the content of the main drug was reduced to 86%, and the content of the impurity salicylic acid-(2-diethylaminoethyl ester) hydrochloride rose to more than 13%. Such results did not meet the general requirements for chemical drug stability. The specific data are shown in Table 2.

TABLE 2

| Items | Time (Month) | | | | |
|---|---|---|---|---|---|
| | 0 | 0.5 | 1 | 2 | 3 |
| Main Drug, % | 99.48 | 99.32 | 97.59 | 94.86 | 86.55 |
| Salicylic acid-(2-diethylaminoethyl ester) hydrochloride, % | 0.51 | 0.67 | 2.38 | 5.09 | 13.35 |
| Acetylsalicylic acid, % | Not detected | Not detected | 0.018 | 0.033 | 0.042 |
| Salicylic acid, % | 0.0028 | 0.0035 | 0.0044 | 0.012 | 0.049 |
| Related substances, % | Not detected | Not detected | Not detected | Not detected | Not detected |

Example 3: Preparation of 2-(Diethylamino)-Ethyl-2-Acetoxybenzoate Hydrochloride Particles (1) 2-(diethylamino)-ethyl-2-acetoxybenzoate hydrochloride obtained in Example 1 was screened with an 80-mesh screen.

(2) Formulation of 1.5% hypromellose solution: 1.5 g hypromellose was dissolved in 100 g hot water, with stirring to homogeneity, and the solution stood overnight at room temperature for standby.

(3) 100 g of 2-(diethylamino)-ethyl-2-acetoxybenzoate hydrochloride pretreated in step (1) was mixed with 1.5 g of hypromellose dry powders, and 9-10 g of hypromellose solution prepared in step (2) was added to mix uniformly, producing a soft material. The soft material was pressed through a 14-mesh screen.

(4) The soft material was dried at 60° C. for 4-6 hours.

(5) The dried soft material was granulated and the particles that could pass through a 10-mesh screen but couldn't pass through a 60-mesh screen were selected.

The resultant particles of 2-(diethylamino)-ethyl-2-acetoxybenzoate hydrochloride were white-like, and had a repose angle of 28°. The pH value of the aqueous solution at 25±0.5° C. was 4.3-4.4.

Example 4: Preparation and Stability Study of Particles of 2-(Diethylamino)-Ethyl-2-Acetoxybenzoate Hydrochloride for Spray 5 g of the particles of 2-(diethylamino)-ethyl-2-acetoxybenzoate hydrochloride prepared in Example 3 were packaged in a high density polyethylene bottle and sealed, and the bottle was placed in a packaging composite bag of polyester/aluminum/polyethylene for drug. Sterile water (50 mL) was used as a solvent (stored in a medicinal glass bottle or a medicinal polyethylene plastic bottle), and was placed in a plastic tray with a pharmaceutical spray pump and the packaged particles. Then, they were together placed in a white card carton. In use, a patient could dissolve 2-(diethylamino)-ethyl-2-acetoxybenzoate hydrochloride particles in sterile water to form a spray for use with a pharmaceutical spray pump.

The above prepared spray particles of 2-(diethylamino)-ethyl-2-acetoxybenzoate hydrochloride (packaged in a high density polyethylene bottle, sealed and placed in a packaging composite bag of polyester/aluminum/polyethylene for drug) were stored at 25° C.±2° C. and 60%±10% relative humidity for 0 month, 3 months, 6 months, 9 months, 12 months. Morphology, dry weight loss, moisture, specific impurities (salicylic acid-(2-diethylaminoethyl ester) hydrochloride, acetylsalicylic acid, salicylic acid), related substances, and the content of main drug were detected. The morphology was determined visually. The moisture was detected by a volumetric titration method (the volumetric titration method of the Fischer-Tropsch method in "Chinese Pharmacopoeia"). The contents of the specific impurities and the main drug were detected by high-performance liquid chromatography (external standard method), and the related substances were detected by adopting a high-performance liquid chromatography (principal component self-control method without correction factors). The conditions of the high performance liquid chromatography were the same as those in Example 2.

The results of the stability study showed that, after the spray particles were placed at 25° C.±2° C. for 12 months, the stability was very good, and various physicochemical parameters were substantially unchanged. The data are shown in Table 3.

TABLE 3

| | Time (Month) | | | | |
|---|---|---|---|---|---|
| Items | 0 | 3 | 6 | 9 | 12 |
| Morphology | White-like particles | White-like particles | White-like particles | White-like particles | White-like particles |
| Dry weight loss, % | 0.53 | 0.43 | 0.44 | 0.44 | 0.49 |
| Moisture, % | 0.33 | 0.14 | 0.19 | 0.16 | 0.21 |
| Salicylic acid-(2-diethylaminoethyl ester) hydrochloride, % | 0.34 | 0.33 | 0.34 | 0.34 | 0.38 |
| Acetylsalicylic acid, % | Not detected | Not detected | Not detected | Not detected | Not detected |
| Salicylic acid, % | 0.0013 | 0.0022 | 0.0025 | 0.0036 | 0.0031 |
| Related substances, % | 0.031 | 0.025 | 0.022 | 0.021 | 0.027 |
| Main drug, % | 99.7 | 99.4 | 99.5 | 99.7 | 99.6 |

Example 5: Synthesis of 2-(Diethylamino)-Ethyl-2-(4-Isobutylphenyl) Propionate Hydrochloride Using dichloromethane as the solvent and N,N-dimethylformamide as the catalyst, ibuprofen and sulfoxide chloride were reacted at an equivalent ratio of 1:1.2 at the reaction temperature of 15-30° C. for 2-4 hours, producing ibuprofen acyl chloride. Dichloromethane was added, 2.0 equivalents of diethylaminoethanol was added, and ibuprofen acyl chloride was slowly added dropwise in the presence of an ice water bath. The temperature was slightly increased during the addition. It was further stirred for 2 hours after the addition. 0.5% dilute aqueous solution of hydrochloric acid was added to terminate the reaction. The mixture was layered. The organic phase was washed with saturated sodium bicarbonate and water, dried over anhydrous sodium sulfate, and the solvent was removed to obtain a crude product of ibuprofen amine. After adding an isopropyl acetate solution containing hydrogen chloride gas, a large amount of white solid was precipitated, and suction filtration was performed to obtain 2-(diethylamino)-ethyl-2-(4-isobutylphenyl) propionate hydrochloride. It was recrystallized with acetone to obtain 2-(diethylamino)-ethyl-2-(4-isobutylphenyl) propionate hydrochloride crystals (powder). The repose angle of the powder was 40°.

The synthesized 2-(diethylamino)-ethyl-2-(4-isobutylphenyl) propionate hydrochloride crystals were taken for NMR characterization, using Bruker AV-500 Superconducting NMR instrument, at a temperature of 300.0K. The solvent was $CDCl_3$. The characteristic data obtained are shown below, proving the structure of the obtained product is consistent with 2-(diethylamino)-ethyl-2-(4-isobutylphenyl) propionate hydrochloride.

$^{13}C$ NMR (500 MHZ, $CDCl_3$): δ8.42, 8.51, 17.92, 22.18, 30.00, 44.78, 44.83, 46.91, 46.97, 49.40, 58.49, 127.04, 129.41, 136.89, 140.87, 173.66.

$^{1}H$ NMR (500 MHZ, $CDCl_3$): δ0.90 (t, 6H, J=7.0 Hz), 1.26 (m, 6H), 1.50 (m, 3H), 1.86 (d, J=7.0 Hz, 1H), 2.44 (m, 2H), 2.85 (d, J=7.0 Hz, 1H), 2.95 (m, 3H), 3.25 (m, 2H), 4.10 (m, 2H), 4.45 (m, 2H), 6.88 (d, 1H, J=7.5 Hz), 7.17 (d, 1H, J=8.0 Hz), 7.55 (d, 1H, J=7.5 Hz), 7.88 (d, 1H, J=8.0 Hz), 12.31 (s, 1H).

Example 6: Stability of Aqueous Solution of 2-(Diethylamino)-Ethyl-2-(4-Isobutylphenyl) Propionate Hydrochloride 10 g of 2-(diethylamino)-ethyl-2-(4-isobutylphenyl) propionate hydrochloride prepared in Example 5 was dissolved in 50 mL of sterile water and placed at 25° C.±2° C. Samples were taken on day 0, week 1, week 2, week 3 and week 4 to detect the contents of the main drug and specific impurities (ibuprofen), wherein the content of the main drug and specific impurities were detected by high-performance liquid chromatography (area normalization). The conditions of HPLC were as follows:

Column: Inertsil ODS-3 (250×4.6 mm, 5 μm) or equivalent

Flow rate: 1.0 ml/min

Column temperature: 33° C.

Wavelength: 264 nm

Injection volume: 10 μl

Mobile phase: (3.065 g sodium acetate+150 ml acetic acid+375 ml water): acetonitrile (35:65).

The results of the stability study showed that after the aqueous solution of 2-(diethylamino)-ethyl-2-(4-isobutylphenyl) propionate hydrochloride was placed at 25° C.±2° C. for 4 weeks, the content of the main drug was reduced to about 89%, and the content of the impurity ibuprofen rose to more than 10%. Such results did not meet the general requirements for chemical drug stability. The specific data are shown in Table 4.

TABLE 4

| Items | Time (week) | | | | |
|---|---|---|---|---|---|
| | 0 | 1 | 2 | 3 | 4 |
| Main drug (%) | 100.00 | 99.51 | 98.12 | 95.83 | 89.76 |
| Ibuprofen (%) | Not detected | 0.39 | 1.69 | 4.04 | 10.03 |
| Unknown peak (%) | Not detected | 0.10 | 0.19 | 0.13 | 0.21 |

Example 7: Preparation of 2-(Diethylamino)-Ethyl-2-(4-Isobutylphenyl) Propionate Hydrochloride Particles (1) 2-(diethylamino)-ethyl-2-(4-isobutylphenyl) propionate hydrochloride obtained in Example 5 was screened with an 80-mesh screen.

(2) 0.5% of carbomer binder was formulated. 1.0 g of carbomer was dissolved in 200 ml of water and allowed to stand for use.

(3) Particles were prepared by fluidized bed. 200 g of the pretreated 2-(diethylamino)-ethyl-2-(4-isobutylphenyl) propionate hydrochloride in step (1) was passed into the fluidized bed (FLZB-3, Chuangzhi Electromechanical Technology Development Co., Ltd.), and the adhesive prepared in step (2) was sprayed to prepare particles. The temperature of the materials was 23-28° C., the inlet air temperature was 60° C., the cylinder temperature was 27° C., and the spraying flow rate was 0.8-2.0 r/min.

The obtained particles of 2-(diethylamino)-ethyl-2-(4-isobutylphenyl) propionate hydrochloride were white-like, with a repose angle of 29°.

Example 8: Preparation and Stability Study of Particles of 2-(Diethylamino)-Ethyl-2-(4-Isobutylphenyl) Propionate Hydrochloride for Spray 10 g of the particles of 2-(diethylamino)-ethyl-2-(4-isobutylphenyl) propionate hydrochloride prepared in Example 7 were sealed in a packaging composite bag of polyester/aluminum/polyethylene for drug. Sterile water (50 mL) was used as a solvent (stored in a medicinal glass bottle or a medicinal polyethylene plastic bottle), and was placed in a plastic tray with a pharmaceutical spray pump and the packaged particles. Then, they were together placed in a white card carton. In use, a patient could dissolve 2-(diethylamino)-ethyl-2-(4-isobutylphenyl) propionate hydrochloride particles in sterile water to form a spray for use with a pharmaceutical spray pump.

The above prepared spray particles of 2-(diethylamino)-ethyl-2-(4-isobutylphenyl) propionate hydrochloride (sealed in a packaging composite bag of polyester/aluminum/polyethylene for drug) were stored at 25° C.±2° C. and 60%±10% relative humidity for 0 month, 3 months, 6 months, 9 months, 12 months. Morphology, dry weight loss, moisture, specific impurity (ibuprofen), and the content of main drug were detected. The morphology was determined visually. The moisture was detected by a volumetric titration method (the volumetric titration method of the Fischer-Tropsch method in "Chinese Pharmacopoeia"). The contents of the specific impurity and the main drug were detected by high-performance liquid chromatography (area normalization). The conditions of the high performance liquid chromatography were the same as those in Example 6.

The results of the stability study showed that, after the spray particles were placed at 25° C.±2° C. for 12 months, the stability was very good, and various physicochemical parameters were substantially unchanged. The data are shown in Table 5.

TABLE 5

| | Time (Month) | | | | |
|---|---|---|---|---|---|
| | 0 | 3 | 6 | 9 | 12 |
| Morphology | White-like particles | White-like particles | White-like particles | White-like particles | White-like particles |
| Dry weight loss, % | 0.50 | 0.48 | 0.45 | 0.54 | 0.48 |
| Moisture, % | 0.28 | 0.24 | 0.29 | 0.18 | 0.20 |
| Ibuprofen, % | 0.31 | 0.53 | 0.34 | 0.24 | 0.25 |
| Unknown peak, % | Not detected | Not detected | 0.14 | 0.15 | 0.22 |
| Main drug, % | 99.69 | 99.47 | 99.52 | 99.61 | 99.53 |

Example 9: Synthesis of Salicylic Acid-(2-Diethylaminoethyl Ester) Hydrochloride and Preparation of Tablets 1. Synthesis of Compounds 2-(diethylamino)-ethyl-2-acetoxybenzoate hydrochloride (31.5 g) obtained in Example 1 was dissolved in acetonitrile (30 mL), and concentrated hydrochloric acid (10 mL) was added, with stirring at room temperature for 48 hours. The solution was concentrated and evaporated to dry, and 50 mL of water was added to dissolve the dried substance. Saturated sodium bicarbonate solution was added with stirring. The solution was extracted with isopropyl acetate, washed with saturated brine, and dried over anhydrous sodium sulfate. It was filtered, and HCl gas was introduced. White solid was precipitated. The solid was recrystallized from ethanol to obtain salicylic acid-(2-diethylaminoethyl ester) hydrochloride (17.7 g, yield: 65%).

HNMR (CDCl$_3$) δ (ppm): 11.31 (br, 1H), 10.47 (s, 1H), 7.87 (dd, J=8.0, 1.5 Hz, 1H), 7.52-7.49 (m, 1H), 7.03 (d, J=8.0 Hz, 1H), 6.95-6.92 (m, 1H), 4.69 (t, J=5.0 Hz, 2H), 3.52 (q, J=4.5 Hz, 2H), 3.24-3.17 (m, 4H), 1.30-1.25 (m, 6H).

2. Preparation of Tablets (1) Salicylic acid-(2-diethylaminoethyl ester) hydrochloride was screened through an 80-mesh screen.

(2) 1.0% of ethyl cellulose solution was formulated. 1.0 g ethyl cellulose was dissolved in 100 g ethanol, with stirring to homogeneity, and allowed to stand overnight at room temperature for standby.

(3) 100 g of the pretreated salicylic acid-(2-diethylaminoethyl ester) hydrochloride in step (1) was mixed with 5.0 g of talc powder, and then 6-8 g of the ethyl cellulose solution prepared in step (2) was added to mix uniformly for achieving a soft material. The soft material was pressed through a 3-mesh screen.

(4) The soft material was dried at 60° C. for 8 hours.

(5) The dried soft material was pressed to obtain tablets.

The tablets of salicylic acid-(2-diethylaminoethyl ester) hydrochloride prepared above were sealed in a high-density polyethylene bottle, and 50 mL of sterile water was used as a solvent (stored in a medicinal glass bottle or a medicinal polyethylene plastic bottle). They were placed in the plastic tray together with a medicinal soft brush, and then were together placed in a white card carton. After a long-term stability study (25° C.±2° C., 12 months), the stability of the tablets was good, and met the requirements of the pharmaceutical industry.

During use, patients could dissolve the tablets of salicylic acid-(2-diethylaminoethyl ester) hydrochloride in sterile water, and an inunction was formed by the medicinal soft brush for use.

The above examples are only preferred embodiments of the present invention and are not intended to limit the scope of the present invention. The essential technical content of the present invention is broadly defined in the scope of the claims. If any product or method found by any other part falls into the scope of the claims, it is an equivalent of the present invention, and should be covered by the scope of the claims

The invention claimed is:

1. A stable pharmaceutical composition containing a non-steroidal anti-inflammatory drug derivative, including at least a separated solid portion and a separated liquid portion,
    wherein the solid portion includes a therapeutically effective amount of a salt, and the liquid portion includes a pharmaceutically acceptable solvent,
    the salt is selected from the group consisting of 2-(diethylamino)-ethyl-2-acetoxybenzoate hydrochloride, salicylic acid-(2-diethylaminoethyl ester) hydrochloride, and 2-(diethylamino)-ethyl-2-(4-isobutylphenyl) propionate hydrochloride,
    the solid portion is in a dosage form selected from the group consisting of powders, tablets and granules comprising a pharmaceutically acceptable binder,
        wherein the pharmaceutically acceptable binder is selected from the group consisting of hypromellose, carbomer, ethyl cellulose, hydroxypropyl cellulose, vinyl cellulose, starch, pregelatinized starch, and polyvinylpyrrolidone,
    the mass ratio of said salt to the pharmaceutically acceptable binder is from 100:0.05 to 100:10,
    the solid portion and the liquid portion are configured to be mixed when the pharmaceutical composition is used so as to form a solution dosage form for external administration, and
    the solid portion is stored in a hermetic, pharmaceutically acceptable packaging material,
    wherein the solid portion is stable after storing at 25° C.±2° C. for 12 months.

2. The pharmaceutical composition according to claim 1, wherein the mass ratio of the solid portion to the liquid portion is from 0.1:100 to 40:100.

3. The pharmaceutical composition according to claim 1, wherein the mass ratio of the solid portion to the liquid portion is from 0.5:100 to 20:100.

4. The pharmaceutical composition according to claim 1, wherein the mass ratio of the solid portion to the liquid portion is from 1:100 to 10:100.

5. The pharmaceutical composition according to claim 1, wherein the mass ratio of said salt to the pharmaceutically acceptable solvent is from 0.1:100 to 40:100.

6. The pharmaceutical composition according to claim 1, wherein the mass ratio of said salt to the pharmaceutically acceptable solvent is from 0.5:100 to 20:100.

7. The pharmaceutical composition according to claim 1, wherein the mass ratio of said salt to the pharmaceutically acceptable solvent is from 1:100 to 10:100.

8. The pharmaceutical composition according to claim 1, wherein the pharmaceutically acceptable solvent is selected from the group consisting of sterile water, decarbonated water, ethanol, sorbitol aqueous solution, and physiological saline.

9. The pharmaceutical composition according to claim 1, wherein the pharmaceutically acceptable binder is hypromellose.

10. The pharmaceutical composition according to claim 1, wherein the mass ratio of said salt to the pharmaceutically acceptable binder is from 100:1 to 100:5.

11. The pharmaceutical composition according to claim 1, wherein the mass ratio of said salt to the pharmaceutically acceptable binder is from 100:1 to 100:2.

12. The pharmaceutical composition according to claim 1, wherein the powders or granules have a repose angle of no more than 40°.

13. The pharmaceutical composition according to claim 1, wherein the powders or granules have a repose angle of no more than 35°.

14. The pharmaceutical composition according to claim 1, wherein the powders or granules have a repose angle of no more than 30°.

15. The pharmaceutical composition according to claim 1, wherein the pharmaceutically acceptable packaging material is selected from the group consisting of a low density polyethylene film, a low density polyethylene bag, a high density polyethylene film, a low density polyethylene bottle, a high density polyethylene bottle, a polypropylene bottle, a poly(ethylene terephthalate) bottle, a polyester/aluminum/polyethylene composite bag, a glass bottle, or a combination thereof.

16. The pharmaceutical composition according to claim 1, wherein the pharmaceutically acceptable packaging material is a combination of a high density polyethylene bottle and a polyester/aluminum/polyethylene composite bag.

17. The pharmaceutical composition according to claim 1, wherein the pharmaceutical composition is provided with a pharmaceutical spray device, a medicinal dropper, a medicinal soft brush, or a combination thereof.

18. The pharmaceutical composition according to claim 1, wherein said solution dosage form for external administration is at least one form selected from the group consisting of a spray, a drop, or an inunction.

19. The pharmaceutical composition according to claim 1, wherein, when the pharmaceutical composition is used, the solid portion is mixed with the liquid portion to form a dosage form for transdermal administration.

20. The pharmaceutical composition according to claim 19, wherein said solution dosage form for transdermal administration is at least one form selected from the group consisting of a spray, a drop, or an inunction.

* * * * *